US006723886B2

(12) United States Patent
Allison et al.

(10) Patent No.: US 6,723,886 B2
(45) Date of Patent: Apr. 20, 2004

(54) USE OF CATALYTIC DISTILLATION REACTOR FOR METHANOL SYNTHESIS

(75) Inventors: Joe D. Allison, Ponca City, OK (US); Harold A. Wright, Ponca City, OK (US); Todd H. Harkins, Ponca City, OK (US); Doug S. Jack, Ponca City, OK (US)

(73) Assignee: ConocoPhillips Company, Houston, TX (US)

( * ) Notice: Subject to any disclaimer, the term of this patent is extended or adjusted under 35 U.S.C. 154(b) by 0 days.

(21) Appl. No.: 10/147,760

(22) Filed: May 16, 2002

(65) Prior Publication Data

US 2002/0177741 A1 Nov. 28, 2002

Related U.S. Application Data

(63) Continuation-in-part of application No. 09/714,675, filed on Nov. 16, 2000.
(60) Provisional application No. 60/291,923, filed on May 17, 2001, and provisional application No. 60/166,025, filed on Nov. 17, 1999.

(51) Int. Cl.$^7$ .............................................. C07C 27/20
(52) U.S. Cl. ...................... 568/909; 568/876; 568/886; 568/891; 568/896; 568/897
(58) Field of Search ................. 568/909, 876, 568/886, 891, 896, 897

(56) References Cited

U.S. PATENT DOCUMENTS

| | | | |
|---|---|---|---|
| 3,427,253 A | 2/1969 | Becker-Boost et al. ..... 252/373 |
| 4,081,253 A | 3/1978 | Marion ...................... 48/197 R |
| 4,439,350 A | 3/1984 | Jones, Jr. .................... 502/527 |
| 4,766,154 A | 8/1988 | Bonnell et al. .............. 518/700 |
| 5,013,407 A | 5/1991 | Nocca et al. ................ 202/158 |
| 5,179,129 A | 1/1993 | Studer ........................ 518/700 |
| 5,449,501 A | 9/1995 | Luebke et al. .............. 422/193 |
| 5,498,318 A | 3/1996 | Alagy et al. ................. 203/29 |
| 5,714,091 A | 2/1998 | Mazanec et al. ............ 252/373 |
| 5,817,906 A | 10/1998 | Marker et al. .............. 585/640 |
| 5,886,055 A * | 3/1999 | Nemphos et al. ........... 518/700 |
| 5,888,376 A | 3/1999 | Wittenbrink et al. ......... 208/59 |
| 5,925,685 A | 7/1999 | Adams et al. .............. 518/700 |
| 5,986,157 A | 11/1999 | Ryu ........................... 585/671 |
| 6,005,150 A | 12/1999 | Vora ........................... 585/324 |
| 6,267,864 B1 | 7/2001 | Yadav et al. ................ 205/341 |

OTHER PUBLICATIONS

Dudukovic, M.P.; *Trends in Catalytic Reaction Engineering*; Catalysis Today 48 (1999) 5–15 (pp. 41).

Mills, G. A.; *Status and Future Opportunities for Conversion of Synthesis Gas to Liqluid Fuels*; Fuel 1994 vol. 73 No. 8; (pp. 1243–1278).

* cited by examiner

*Primary Examiner*—Alan L. Rotman
*Assistant Examiner*—Héctor M. Reyes
(74) *Attorney, Agent, or Firm*—Conley Rose, P.C.

(57) ABSTRACT

An apparatus and method is disclosed for producing alcohols, particularly methanol, according to an alcohol synthesis process. The apparatus comprises a catalytic distillation reactor where reactants are fed into the catalytic distillation reactor to undergo catalytic reaction to form methanol. Methanol production beyond the thermodynamic limit is achieved in the apparatus through use of multiple distillation stages, preferably at least three.

10 Claims, 3 Drawing Sheets

USE OF CATALYTIC DISTILLATION REACTOR FOR METHANOL SYNTHESIS

CROSS-REFERENCE TO RELATED APPLICATIONS

The present application claims the benefit of priority from U.S. provisional application Ser. No. 60/291,923, filed May 17, 2001, entitled "Use of Catalytic Distillation Reactor for Methanol Synthesis. Further, the present application is a continuation-in-part application of U.S. utility application Ser. No. 09/714,675, filed Nov. 16, 2000, and entitled "Catalytic Distillation Reactor", which claims the benefit of 35 U.S.C. 111(b) provisional application Ser. No. 60,166,025 filed Nov. 17, 1999, and entitled "Catalytic Distillation Reactor for Fischer-Tropsch Synthesis". Each of the above-listed applications is hereby incorporated herein by reference for all purposes.

STATEMENT REGARDING FEDERALLY SPONSORED RESEARCH OR DEVELOPMENT

Not applicable.

FIELD OF THE INVENTION

The present invention relates to a method and apparatus for converting synthesis gas, i.e., a mixture of carbon monoxide and hydrogen, to alcohols, particularly methanol. Particularly this invention relates to the use of a catalytic distillation reactor to achieve both reaction of the syngas and high net conversion. High net conversion occurs through use of multiple distillation stages within the reactor to achieve net conversion beyond the thermodynamic limit for a single stage.

BACKGROUND OF THE INVENTION

Large quantities of methane, the main component of natural gas, are available in many areas of the world. Methane can be used as a starting material for the production of alcohols. The conversion of methane to alcohols is typically carried out in two steps. In the first step methane is reformed with water or partially oxidized with oxygen to produce carbon monoxide and hydrogen (i.e., synthesis gas or syngas). In a second step, the syngas is converted to alcohols.

This second step, the preparation of alcohols from synthesis gas is well know in the art and is an example of carbon monoxide hydrogenation reactions. A variety of reactions can produce alcohols from synthesis gas. Methanol synthesis is a very common reaction. Further, the Fischer Tropsch reaction also produces alcohol by-products. The Fischer-Tropsch reaction conventionally involves the catalytic hydrogenation of carbon monoxide to produce a variety of products ranging from methane to higher alkanes. Catalysts for use in synthesis of these various products from synthesis usually depend on the desired product. Catalysts for the production of hydrocarbons usually contain a catalytically active metal from one of the Groups 8, 9, or 10 (in the New notation of the periodic table of the elements, which is followed throughout). Group 8, 9, and 10 metals have also been used in catalysts for the production of alcohols, catalysts for the production of alcohols. However, catalysts for the production of alcohols, particularly methanol, typically are copper-based, many containing copper in the form of an alloy, such as copper-zinc alloys and copper-rare earth alloys. The catalysts may additionally contain one or more promoters. Promoters for copper-zinc catalysts include Cr, Al, Mn, V, and Ag, among others.

Traditional methods of Fischer-Tropsch synthesis produce a range of products. In a methanol synthesis process, by-products may include hydrocarbons, higher alcohols, dimethyl ether, esters, ketones, and aldehydes. The range of hydrocarbons based on the carbon chain length of the hydrocarbon is discussed in U.S. Pat. No. 4,619,910, which is incorporated herein by reference. This well-known distribution is known as the Anderson-Schulz-Flory distribution. In general, the range of hydrocarbons produced in Fischer-Tropsch processes may be characterized by the Anderson-Schulz-Flory distribution with a suitable value for the parameter alpha, regardless of catalyst type.

Because of the range of products, typical systems that use the Fischer-Tropsch process provide a separation stage that follows the reaction stage. The separation stage is often one or more distillation columns. The distillation columns separate the product into fractions according to boiling point. The lighter products, having lower boiling points, will vaporize and pass to the overhead region of a distillation column, where they can be removed as one product stream. The heavier products, having higher boiling points, will condense and fall to the lower region of the distillation column, where they can be removed as a separate product stream. In addition, any one or more of the product streams having intermediate compositions can be removed from the column at intermediate points between the top and the bottom and may then be sent to other columns for further separation if desired. In this way, in a process for producing methanol, the methanol may be separated from undesired by-products.

Water can also be also produced during Fischer-Tropsch synthesis. Recent research indicates that water can deactivate a Fischer-Tropsch catalyst in certain circumstances. Rothaemel, Hanssen, Blekkan, Schanke and Holmen, *The Effect of Water on Cobalt Fischer-Tropsch Catalysts Studied by Steady-State Isotropic Transient, Kinetic Analysis,* 38 Catalysts Today 79–84(1997); Schanke, Hilmen, Bergene, Kinnari, Rytter, Adnanes and Holmen, *Reoxidation and Deactivation of Supported Cobalt Fischer-Tropsch Catalysts,* Energy & Fuels, Vol. 10 No.4(July/August 1996) p. 867–872.

In addition, the catalytic methanol synthesis as with the Fischer-Tropsch synthesis, when practiced on a commercial scale, generates heat that must be removed from the reaction vessel. Methanol and Fischer-Tropsch synthesis reactions are highly exothermic, and reaction vessels must be designed with adequate heat exchange capacity. Large scale reactors, which potentially offer the economic advantages that come with higher volumes, must presently include, at significant cost, sufficient heat transfer equipment within the reactor to remove the heat generated during the reaction. The traditional method for doing this, and a method that may be used in the present invention, is to place heat removal equipment inside the reaction vessel. A typical internal heat removal arrangement comprises a system of tubes within one or more reaction chambers. The tubes contain a fluid such as water, or any other acceptable fluid, which acts as the heat exchange medium. In operation, the heat generated within the reaction chamber passes through the heat exchange tubes and heats the fluid therein. The heat exchange fluid is then pumped outside the reaction vessel, where the heat is released, preferably through a heat exchanger. This process can be carried out continuously, with the heat exchange fluid circulating through the reaction chamber. A shortcoming of the internal heat exchange process is that the internal heat exchange tubes occupy reactor space. Internal heat removal equipment may therefore decrease the reactor volume that is available for Fischer-Tropsch synthesis, thus limiting the capacities and efficiencies for a given reactor.

The conversion of natural gas to methanol via syngas is a widely used industrial process. Heat integration and recovery are desirable features of the process. For example, methanol is manufactured in large amounts due to its use in a variety of applications, including: a feedstock for other chemicals, fuel use, and other direct uses as a solvent, antifreeze, inhibitor, or substrate. Further, there is a wide range of more specific uses, as described below.

According to one application, methanol is used as a solvent in automobile windshield washer fluid and as a cosolvent in various formulations for paint and varnish removers. It is also used as a process solvent in chemical processes for extraction, washing, crystallization, and precipitation. For example, methanol is used as an "antisolvent" for precipitation of polyphenylene oxide after its polymerization. It should be pointed out here that there have been active studies in using the extracts of agricultural plants in medicine. Methanol is often used for the extraction. Methanol extracts of some plants show antibacterial activities. This provides a potential use of methanol in traditional medicine.

According to another application, methanol is used as antifreeze because it has a high freezing point depression ability. It depresses the freezing point of water by 54.5° C. for a 50–50 wt % methanol-water mixture. The largest antifreeze use of methanol is in the cooling system for internal combustion engines. However, the antifreeze market for methanol has been saturated. Its market share has been lost to ethylene glycol since 1960 because of the superior performance of the glycol.

According to yet another application, methanol finds some use as an inhibitor. It inhibits formaldehyde polymerization and is present in paraformaldehyde. Methanol can also serve as a hydrate inhibitor for natural gas processing.

According to still another application, methanol is an inexpensive source of carbon. For this reason, it is a substrate used in may applications for supplying the energy needed for the growth of microorganisms. For example, single-cell protein, a protein in a variety of microbial cells, is produced through fermentation using hydrocarbon substrates, such as methanol. Methanol is also often chosen as the energy source for sewage treatment.

Further, in addition to present uses, new uses such as alternative automobile fuel, supplemental gas turbine fuel at peak demand of electricity, $H_2$ for fuel cells, fuel and cooling system for hypersonic jets, CO and $H_2$ for chemical processes and material processing involve dissociated methanol.

The trend in methanol production has been toward larger capacity and improved energy efficiency. However, thermodynamic equilibrium conditions limit the obtainable conversions of CO and $CO_2$ to methanol according to Equation 2 and Equation 3.

$$CO + 2H_2 \Leftrightarrow CH_3OH \qquad (2)$$

$$CO_2 + 3H_2 \Leftrightarrow CH_3OH + H_2O \qquad (3)$$

On technically performing methanol synthesis accurate matching of temperature, pressure, concentration and catalyst activity are desirable to obtain maximum yields and optimum economics in view of the conversion limitation imposed by the equilibrium. In order to achieve production beyond the thermodynamic limit, conventional methanol production uses multiple reactors, typically with un-reacted feed from one reactor passed to a following reactor. Methanol is typically separated in still another separator apparatus separate from the reactors.

Demand for methanol as a chemical raw material is rising. Further, methanol may play a significant role as a source of energy in the future. Still further, raw materials are becoming less available and more costly. Thus, it is desirable to provide an improved methanol production process that would obtain a higher yield of desired products in a single reactor.

Thus, notwithstanding the foregoing patents and teachings, there remains a need for a continuous methanol synthesis by which the production of certain alcohols can be maximized and controlled.

The present invention overcomes the deficiencies of the prior art.

SUMMARY OF THE INVENTION

The present invention provides a method for producing alcohols from synthesis gas. Particularly, the invention provides the use of a catalytic distillation reactor for methanol or higher alcohol synthesis. In a preferred method, a catalytic distillation reactor is used as a single apparatus to simultaneously achieve both reaction to form at least one alcohol from synthesis gas starting materials and the separation of the alcohol product into various product streams. In a more preferred method, a catalytic distillation reactor is used as a single apparatus to simultaneously achieve both the reaction of synthesis gas and the production of methanol, with a net conversion beyond the thermodynamic limit. Alternately, or in combination, the present method may be used in more general operations to produce other alcohols with similar thermodynamic limitations to methanol.

In a preferred embodiment of the present invention, a process for producing methanol includes contacting synthesis gas with a catalyst in a reaction chamber in a catalytic distillation reactor operating at methanol conversion-promoting conditions. This catalyst can be in a solid or liquid phase. The method may include removing methanol from the reaction chamber. The method may include contacting synthesis gas with catalyst in addition reaction chambers in the catalytic distillation unit. Preferably the contacting occurs in at least three reaction chambers, more preferably at least four reaction chambers, most preferably at least five reaction chambers. Further, the method includes selecting the conversion-promoting conditions in each reaction chamber such that methanol is produced with an optimized yield.

According to some embodiments of the present invention, a method of producing methanol has the advantage of providing net conversion of synthesis gas to methanol beyond the thermodynamic limit, while simultaneously separating methanol from reaction by-products, in a single reaction vessel.

Thus, the present invention comprises a combination of features and advantages that enable it to overcome various problems of methanol production. The various characteristics described above, as well as other features, objects, and advantages, will be readily apparent to those skilled in the art upon reading the following detailed description of the preferred embodiments of the invention, and by referring to the accompanying drawings.

Other objects and advantages of the invention will appear from the following description. For a better understanding of this invention, reference is made to the detailed description thereof which follows, taken together with the subjoined claims.

BRIEF DESCRIPTION OF THE DRAWINGS

For a detailed description of a preferred embodiment of the present invention, reference will now be made to the accompanying drawings, which form a part of the specification, and wherein.

DETAILED DESCRIPTION OF THE INVENTION

As described in detail below, a preferred embodiment of the present invention includes a producing an alcohol from synthesis gas in a reaction vessel that includes a catalyst for driving the reaction and an apparatus and method for continuously separating and recovering the reaction products. The vessel also allows for the continuous feed of various feedstocks into the vessel and for the continuous removal of heat from the vessel.

According to an embodiment of the present invention, methanol is produced from syngas in a reaction vessel that operates as a catalytic distillation unit (CDU). Methanol is preferably produced from synthesis gas in a columnar reactor with a fixed bed catalyst system. Conditions for operation range from older high temperature/high pressure (4500 psi) reactors to current low temperature/low pressure reactors (1500 psi). The CDU is ideally suited for diverse conditions, where temperature and pressure may greatly vary. In a preferred embodiment, the CDU operates at low-pressure and one pass conversion, in one reaction chamber, as described further below, is typically limited to between 40–60%. This is thermodynamically driven due to the equilibrium expression wherein methanol reverts back to syngas at the reaction conditions. Preferably the CDU operates with at least three reaction chambers, or stages, more preferably at least four stages, most preferably at least five stages.

By removing the product methanol between stages in the CDU, the following are realized. First, the removal and quenching of methanol will prevent the reverse reaction to reactant syngas and second, the equilibrium will then be forced to the right to produce additional methanol. Given enough stages in the CDU, the final CO conversion can approach 100%. For example, assuming a 50% conversion at each stage, a 4-stage process will have an overall conversion of 94%. Additionally, the return of the unreacted reactants by distillation to the catalyst zone allows the opportunity to achieve the most complete conversion of the reactants.

Another advantage is the ability to control temperature across the reactor and lower pressure reaction conditions. Temperature control is desirable due to the exothermic nature of the reaction and the temperature sensitivity of low-pressure catalysts. Still another advantage is lower pressure reaction conditions than in conventional methanol synthesis. Apart from the economic benefit of lower reactor and compression costs, low pressure reaction conditions will enable a diluent gas to be used. The diluent gas will lower the partial pressure of the reactant gases, but will help moderate the reaction temperature across the reactor. Further, the use of nitrogen as a diluent gas may allow for oxygen-enriched air to be used in the syngas reactor, thus precluding the need for an air separation unit.

Vessel

Figure 1:
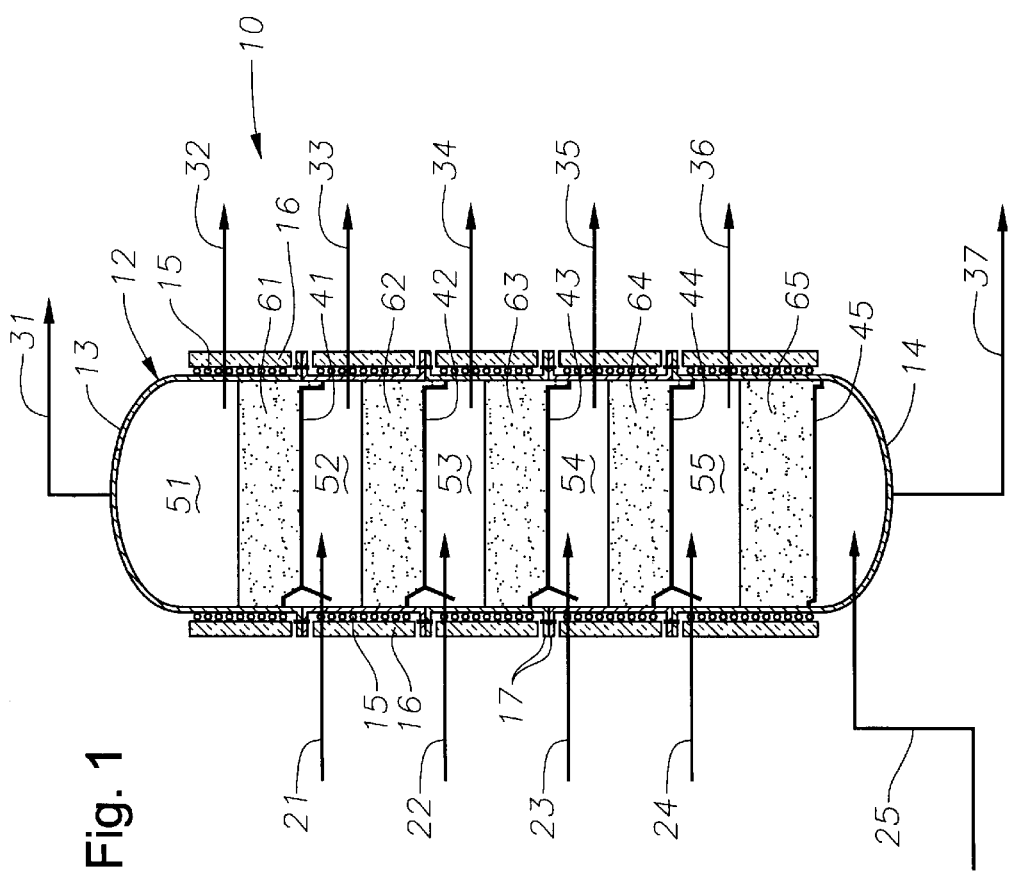
FIG. 1 is a schematic view of an embodiment of a catalytic distillation reactor constructed in accordance with the present invention.

Referring initially to FIG. 1, a preferred embodiment of the present catalytic distillation reactor 10 includes a reaction vessel 12, which generally follows the shape of any of the various distillation columns and mass transfer reactors well known in the art. According to one preferred embodiment, the reactor is generally tubular or cylindrical. The interior of reaction vessel 12 is substantially in the form of a capped hollow tube. During operation, the reaction vessel 12 typically rests in an upright position. Reaction vessel 12 may also conform to other shapes and configurations such as square, oval or rectilinear. Reaction vessel 12 may preferably be formed of multiple cylindrical sections. In this configuration, each of the multiple cylindrical sections includes a flange at each end so that the sections can be bolted together to form the overall reaction vessel 12 of FIG. 1. Caps 13 and 14, disposed on the upper and lower end of the reaction vessel, respectively, act to seal the reaction vessel 12 so that it can be pressurized to conversion-promoting conditions. Reaction vessel 12 is typically constructed of any material capable of withstanding the temperatures and pressures encountered in alcohol synthesis. In one preferred embodiment, reaction vessel 12 is constructed of carbon steel.

Figure 2:
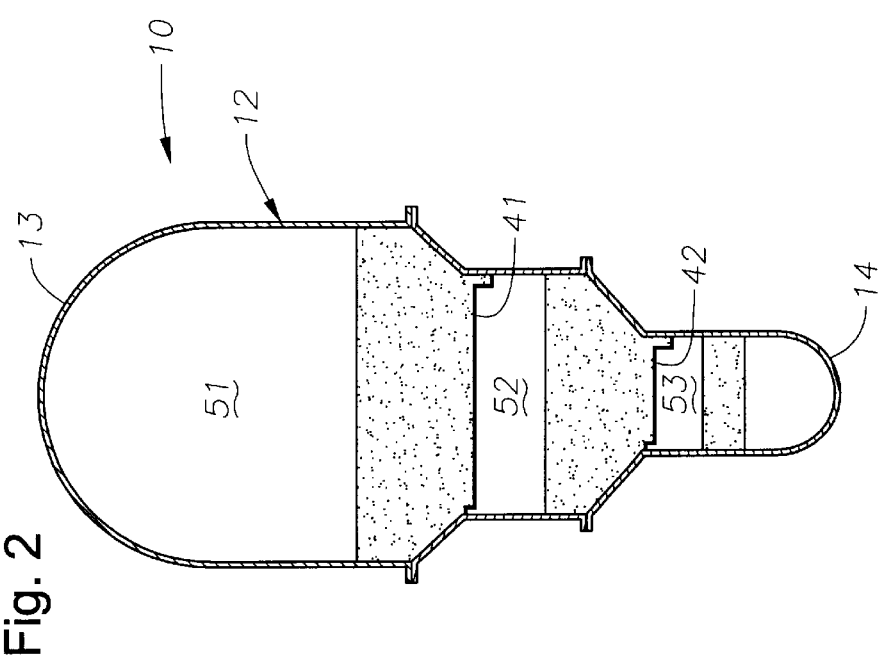
FIG. 2 is a schematic view of an alternative embodiment of the present reaction vessel having different diameters at different vertical positions on the reaction vessel.

In an alternative embodiment shown in FIG. 2, the diameter of reaction vessel 12 varies with vertical position. The reaction vessel shown in FIG. 2 has three horizontal sections with different diameters. As is well known in the art, a distillation column may be designed to have an upper region having a larger diameter than a lower region of the distillation column. This is done to facilitate the expansion and flow of lighter gases in the upper region of the column. In FIG. 2, three reaction zones 51, 52, 53 are shown, although it will be understood that more or fewer zones could be created, having different or similar dimensions. Because the reactors may be shapes other than cylindrical, as used herein, the word "diameter" will mean, without limitation, the traditional diameter of a circle as well as any analogous measurements for different shapes (e.g., the diagonal length of a square).

Positioned inside of reaction vessel 12 of FIG. 1 are a plurality of trays 41, 42, 43, 44, and 45, which define the lower boundaries of a plurality of reaction chambers 51, 52, 53, 54, and 55, respectively. In a preferred embodiment, trays 41, 42, 43, 44, and 45 conform substantially to the interior dimensions of said reaction vessel. It is also preferred that each tray lie in a substantially horizontal position within reaction vessel 12, although it is contemplated that the trays can be inclined. Trays 41, 42, 43, 44, and 45 can be constructed of any material suitable for use in a chemical reactor, including carbon steel. Trays 41, 42, 43, 44, and 45 are typically fastened to the interior of the reaction vessel 12 by conventional mechanical means, such as, but not limited to, bolts, welds, screws, pins, hangers, and interlocking fittings.

Although as shown in FIG. 1 the positions of the individual trays 41, 42, 43, 44, and 45 correspond to the ends of the vessel segments, it will be understood that trays 41, 42, 43, 44, and 45 can be set at varying and adjustable vertical positions within reaction vessel 12. The reaction chambers 51–55 represent individual regions within the reaction vessel 12 in which simultaneous operations of reaction and physical separation take place. It is not necessary that the reaction chambers 51, 52, 53, 54, and 55 be equal in height. Similarly, other embodiments may have a different number of reaction chambers than that shown and the reaction chambers may each have different configurations as explained below.

Passageways through or around trays 51–55 may be provided by a series of bubble caps, downcomers, weirs, filters, sieves, sintered metal sieves, and/or other standard items that are typically used for mass transfer of gaseous and liquid materials in a distillation column. Other materials commonly used in distillation columns to assist in the distillation process may be used in reaction vessel 12 as a matter of engineering design choice and optimization. Some examples of such materials are baffles, plastic or metal saddles, and rings.

Furthermore, according to the present invention, each tray may have any one of several distinct configurations. For example, one or more trays may consist of a metal tray and bubble caps. Other trays may include a filter or sieve structure. Not every tray needs to have the same configuration and, in one preferred embodiment, each tray has a configuration that has been optimized for the particular reaction/separation combination to be performed on that tray.

Positioned above trays 41–45 are catalytic materials 61, 62, 63, 64, and 65, respectively. The catalytic materials preferably comprise all of the necessary components of a alcohol synthesis catalyst or catalyst system. Thus, active catalyst components such as catalytically active metals for alcohol synthesis and their precursor and derivative compounds, are included within the definition of "catalytic material" as used herein. Support materials such as aluminas, silicas, and other catalyst support materials, as are well known in the art, are likewise included within the definition of "catalytic material" as used herein. Promoters, activators, and other materials that facilitate catalysts are also included within the definition of "catalytic material".

While catalytic materials 61–65 are shown occupying less than all of the volume of their respective chambers, the volume of the catalytic materials may be increased or decreased. For example, in some embodiments, the catalytic material fills each chamber. It is further contemplated that, in some configurations, the catalyst may be supported on a packing material or other support that is also capable of functioning as a distillation packing, so as to enhance separation. Alternatively, non-catalytic distillation packing or the like (not shown), can be used in conjunction with the catalytic material(s) 61–65. In this case, the distillation packing can be used above one or more portions of catalytic material, or can be mixed with the catalytic material. Additionally and alternatively, the distillation packing, whether catalytic or non-catalytic, may be dump packed or structurally packed.

A plurality of feed lines 21, 22, 23, and 24 are preferably provided for feeding the desired gases into reaction vessel 12. Although four feed lines are shown, any number of feed lines, more or fewer than four, may be used. Preferably, each of the feed lines 21–24 enters the reaction vessel 12 into one of the reaction chambers 52–55, respectively, as shown in FIG. 1. In other embodiments, feed lines 21, 22, 23, and 24 may be positioned according to a variety of configurations so as to achieve certain desired effects. For example, all feed lines may enter the reaction vessel in one reaction chamber. Compressors, heaters, and the like (not shown) can be provided on feed lines 21–24, so that the feed materials can be preheated and pressurized if desired. For example, it may be desired to preheat and pressurize the feed materials such that they enter the reactor at conditions compatible with those of the reaction vessel 12 at their point of entry.

According to a preferred embodiment, the reaction/separation products exit reaction vessel 12 through on or more of product lines 31, 32, 33, 34, 35, 36, and 37. The compositions of the various products passing through these product lines will vary depending on operating parameters, as described below.

Still referring to FIG. 1, a plurality of heating coils 15 are preferably positioned around reaction vessel 12. Heating coils 15 may be selected from among the heating coils commonly used in the art for reactors and distillation columns. Insulation 16 is positioned around heating coils 15 and is preferably placed around the exterior of reaction vessel 12 and coils 15 as shown in FIG. 1. A separate heating coil 15 is preferably disposed around each individual reaction chamber 51, 52, 53, 54, and 55 and each coil 15 is preferably individually controlled so as to maintain each of the reaction chambers at a specific desired temperature.

Figure 3:
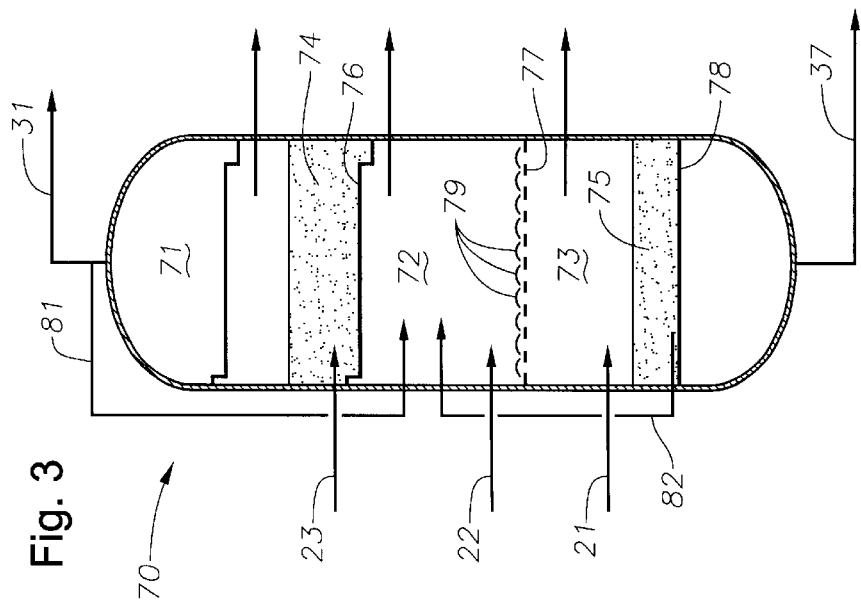
FIG. 3 is a schematic view of a second alternative embodiment of the present reaction vessel configured such that one reaction chamber contains no catalyst material.

In the embodiment shown in FIG. 1, a catalytic material 61–65 is present in each of the reaction chambers 51–55. In other embodiments of the present invention, however, one or more reaction chambers 51–55 may have no catalyst material present. By way of illustration and not limitation, in such an embodiment, any tray and its associated reaction chamber that does not contain catalytic material, would be configured to act essentially as a stage of a distillation column. FIG. 3 shows a reaction vessel 70 configured so that one reaction chamber 72 does not contain a catalyst material. As shown in FIG. 3, alcohol synthesis occurs in a lower reaction chamber 73 of the reaction vessel 70. The conditions present in lower reaction chamber 73 (the temperature, pressure, catalyst material, etc.) are chosen to optimize alcohol synthesis consistent with the relative position of reaction chamber 73 in the reaction vessel 70. Catalyst material 75 in reaction chamber 73 rests on tray 78 or is otherwise supported. Lighter alcohols move upward from reaction chamber 73. These alcohols may be moved upward through a series of pure distillation stages that contain no catalyst material, such as reaction chamber 72. Reaction chamber 72, defined by trays 76 and 77, contains no catalyst material, and distillation in reaction chamber 72 is achieved through bubble caps 79 that are positioned on tray 77. Once the lighter alcohols reach an upper region of reaction vessel 70, the alcohols encounter a new set of conditions that promote alcohol synthesis in reaction chamber 71, which contains catalyst material 74. Reaction chamber 71 has conditions chosen to optimize methanol synthesis in the relative position of upper reaction chamber 71. While the lighter alcohols migrate to upper regions of the reaction vessel 70, heavier alcohols move in the opposite direction to the lower areas of the reaction vessel 70. Thus, the individual reaction chambers in the present device can be uniquely tailored to promote alcohol synthesis for the kinds of alcohols that predominate in each such reaction chamber.

Figure 6:
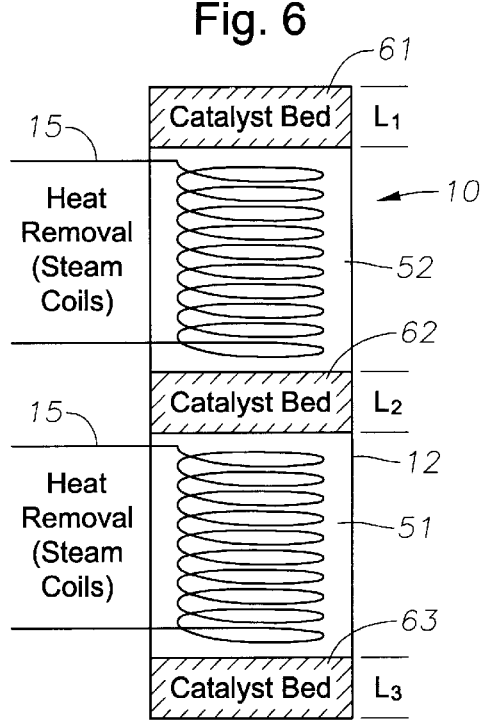
FIG. 6 is a view of a fifth embodiment of the present reaction vessel having catalyst beds which may be of varying thickness.

Referring now to FIG. 6, a catalytic distillation reactor 10 is provided in which layers of catalyst material 61, 62, 63 of varying thickness are staged between distillation/heat removal chambers 51, 52. The thickness of the catalyst materials 61, 62, 63 may be varied such as to control the reaction and the temperature rise within the distillation/heat removal chambers 51, 52. Any excess heat would be removed by the heat removal coils 15, which may consist of steam coils or any other acceptable heat removal system which is well known in the art. The heat removed from the chambers may then be disposed of by any acceptable means (e.g., inter-process heat exchange (not shown)).

Figure 7:
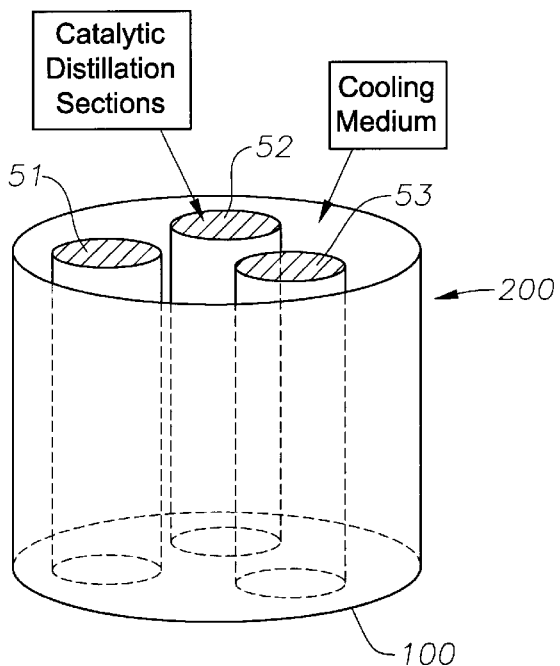
FIG. 7 is a view of a plurality of the present reaction vessels running in parallel and surrounded by a common cooling medium.

Referring now to FIG. 7, a catalytic distillation reactor segment is provided having a plurality of reaction chambers 51, 52, 53 running in parallel inside of an outer shell 100. Within the outer shell 100 and external to the reaction chambers 51, 52, 53 is provided a cooling medium which may be any acceptable cooling medium as is well known in the art (e.g., steam). Preferably, the distillation reactor segment 200 is adapted to be stacked on other distillation reactor segments and would contain mechanisms for product removal (such as those shown in FIG. 1, reference nos. 31–37), liquid redistribution (such as those shown in FIG. 3, reference nos. 81 and 82), and gas/liquid feed streams (such as those shown in FIG. 1, reference nos. 21–24).

Figure 8:
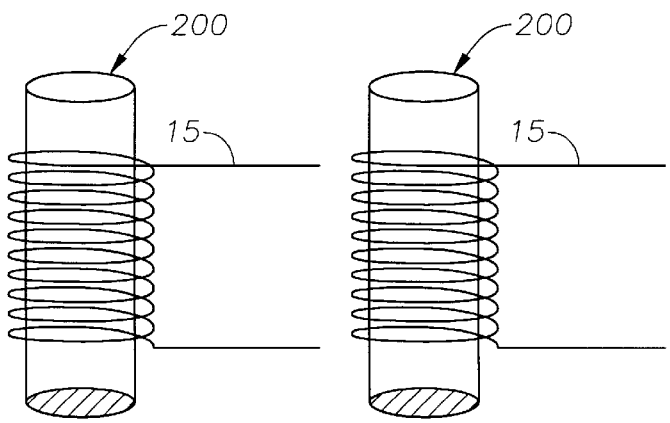
FIG. 8 is a view of a plurality of the present reaction vessels running in parallel and surrounded by individual cooling units.

Referring now to FIG. 8, a plurality of catalytic distillation reactor segments 200 are run in parallel, each with separate external heat removal units 15 for temperature control. Preferably, the distillation reactor segments 200 are adapted to be stacked on other distillation reactor segments and would contain mechanisms for product removal (such as those shown in FIG. 1, reference nos. 31–37), liquid redistribution (such as those shown in FIG. 3, reference nos. 81 and 82), and gas/liquid feed streams (such as those shown in FIG. 1, reference nos. 21–24).

Other common features of distillation columns may be incorporated into the design of the present reaction vessel. These include manholes or manways, which provide access to the interior and facilitate cleaning of the vessel, and inspection ports or windows to permit visual inspection of the interior of the reaction vessel while in use. It is also common practice to provide gangways or ladders on the exterior of the catalytic distillation reactor to permit physical access to all parts of the catalytic distillation reactor.

Catalysts

Catalytic materials 61–65 may be present in different amounts, concentrations, forms and configurations in each of the reaction chambers 51–55. The presence of any mechanical apparatus necessary to position the catalyst material within the column will be understood and will not be further recited herein. Such a mechanical apparatus may include, by way of illustrative example only, catalyst containers, holders, baskets, racks, or nets. Similarly, any suitable configuration may be employed for catalytic materials 61–65. For example, fixed bed, fluidized bed, slurry phase, slurry bubble column, or ebulliating bed systems, among others, may be used. The catalyst can even be in the liquid phase itself. Accordingly, the size and physical form of the catalyst materials 61–65 may vary depending on the reaction chamber in which they are to be used.

The catalytic distillation reactor of the preferred embodiment is preferably used with catalysts active for alcohol synthesis, preferably methanol synthesis. However, there is no particular catalyst type that must be used in the reaction vessel; indeed, reaction vessel 12 may be used with any of the Fischer-Tropsch or alcohol synthesis catalysts now commonly used in alcohol synthesis reactors, or with other types of catalysts. In a similar vein, the preferred embodiment may operate with any physical form of the catalyst, or as it is sometimes called, the catalyst system. In other words the catalytic distillation reactor will function with packed bed, slurry bed, or other types of catalysts.

According to one preferred embodiment, the active catalyst components present in the catalyst materials include any metal known to be active for the production of an alcohol. The active catalyst component is preferably be chosen to favor methanol production. By way of illustration and not limitation, these active metals include Cu—Zn, Cu—Zn alloys promoted with any one or combination of Cr, Al, Mn, V, and Ag, Cu—rare earth alloys, where rare earths include Group 3 elements (e.g. Ce, La, and Th, and the like), and Group 8, 9, and 10 elements (e.g. rhodium) and promoted Group 8, 9, and 10 elements (e.g. rhodium promoted with molybdenum). Alternatively, the active catalyst component may be chosen to favor higher alcohol production (ethanol, propanol, butanol, and the like). By way of illustration and not limitation these active metals include metals active for methanol production promoted with alkali metals.

Active catalyst components used in the catalyst material of the preferred embodiment may be in the form of a sponge, such a Raney™ catalysts available from W. R. Grayce. Alternatively, active catalyst components may be carried or supported on any suitable support. Conventional catalyst supports include but are not limited to supports selected from the group including silica, titania, titania/alumina, zirconia, alumina, aluminum fluoride, and fluorided alumina, silica, titania, titania/alumina, and combinations thereof. Other supports, well known in the art, may also be used. Aluminum fluoride supports are defined as at least one aluminum fluoride (e.g., alpha-$AlF_3$, beta-$AlF_3$, delta-$AlF_3$, eta-$AlF_3$, gamma-$AlF_3$, kappa-$AlF_3$ and/or theta-$AlF_3$).

A preferred form of the desired catalyst material may be prepared by any of the methods known to those skilled in the art. By way of illustration and not limitation, such methods include co-precipitation of the catalytic metals to form an unsupported catalyst, impregnating the catalytically active compounds or precursors onto a support, extruding one or more catalytically active compounds or precursors together with support material to prepare catalyst extrudates, and/or precipitating the catalytically active compounds or precursors onto a support. Accordingly, the supported catalysts of the present invention may be used in the form of powders, particles, pellets, monoliths, honeycombs, packed beds, foams, and aerogels. For example, honeycomb catalysts are further described in concurrently filed U.S. utility application Ser. No. 10/150,327, Attorney Docket Number 1856–10401, entitled "Honeycomb Monolith Support for Catalytic Distillation Reactor", which claims the benefit of priority from U.S. provisional application Serial No. 60/291, 922, filed May 17, 2001, each of which is hereby incorporated herein by reference.

The most preferred method of preparation may vary among those skilled in the art, depending for example on the desired catalyst particle size. Those skilled in the art are able to select the most suitable method for a given set of requirements. The method may include activation of the catalyst prior to use by reduction in hydrogen.

As stated above, the catalyst material, its physical form, and the concentration of its contents can be optimized in each reaction chamber so as to result in a desired reaction scheme. Indeed, the catalyst material should be selected for each reaction chamber so as to optimize the reactions occurring in said reaction chamber.

The recycling or refluxing of materials is common in distillation columns and is also part of a preferred embodiment. One or more recycle lines or reflux lines may take materials from any reaction chamber and return the materials to the reaction vessel 12 at another point. Preferably, as shown in FIG. 3, a recycle stream 81 will take product from the top reaction chamber and deposit the product at a lower point of the reaction vessel 12. Once returned to a relatively lower position of the reaction vessel 12, the recycled light alcohols that were present in the top reaction chamber 51 may undergo additional reaction. Also as shown in FIG. 3, reflux line 82 may remove product from a lower reaction chamber and deposit the product in a higher reaction chamber. As will be understood, the recycle and reflux lines 81, 82 may be configured in a number of ways (not shown). A recycle line 81 or reflux line 82 may merge with one or more feed lines 21–24 as one way of returning products to the reaction vessel 12. In another embodiment, a reflux or recycle line may directly reenter the reaction vessel 12 as shown in FIG. 3. Further, the recycle lines 81 may diverge from one or more product lines 31–37, as shown, as a way of returning fluids found in the product lines to the reaction vessel 12. While in a recycle line 81, fluids may undergo heating, cooling, pressurization, or depressurization as needed to place the products in a physical condition appropriate for return to the reaction vessel 12.

Operation

In operation, reactants and other processing materials, if any, preferably enter reaction vessel 12 through feed lines 21, 22, 23, and 24. The reactants typically used to form alcohols according to the alcohol synthesis process comprise hydrogen, $H_2$ and carbon oxide. The carbon oxide is selected from among carbon monoxide, CO, carbon dioxide, $CO_2$, and combinations thereof. Preferably, $H_2$ and carbon oxide are combined and injected into the reaction vessel together as syngas through each of the feed lines 21, 22, 23, and 24. Alternatively, the reactants $H_2$ and carbon oxide may be individually injected into reaction vessel 12 through one or more of the feed lines 21–24. According to one preferred embodiment, one or more $H_2$/carbon oxide feedstock mixtures enter reaction vessel 12 at multiple points through feed lines 21, 22, 23, and 24. The $H_2$/carbon oxide molar ratio may vary for each of feed lines 21, 22, 23, and 24, where the $H_2$/carbon oxide molar ratio is the ratio of hydrogen molecules to carbon atoms. The molar ratio of hydrogen to carbon oxide may also be varied between the streams entering reaction chambers 51–55, so as to control the alcohol product distribution. Similarly, other conditions related to feed lines 21, 22, 23, and 24 such as flow rate, temperature, and pressure may vary for each particular feed line.

Nitrogen, which is not a raw material for the alcohol synthesis, is typically used as a purge gas when starting up or shutting down reaction vessel 12 before and after a alcohol synthesis run. Nitrogen, which is an inert element and will not react with the reactants or products typically found during alcohol synthesis, is pumped into the reaction vessel 12. The nitrogen purges vessel 12 by displacing any materials that are in the reaction vessel 12. Nitrogen may be fed into reaction vessel 12 through feed lines 21, 22, 23, and 24, or through any combination of these feed lines. Preferably nitrogen is admitted to reaction vessel 12 through a dedicated nitrogen line 25 as shown in FIG. 1.

The concentrations of feed materials and their injection points, the reaction temperatures and pressures, and the catalyst types and amount of catalyst used in various reaction chambers 51–55 in reaction vessel 12 may all be varied in accordance with the present invention to control the product distribution, conversion, and selectivity. Generally speaking, the product lines disposed in the bottom or lower end of reaction vessel 12 will remove heavier (larger chain alcohols) reaction products. Product line 37 may also remove heavier alcohol by-products. Progressively lighter alcohols will pass to progressively upper reaction chambers of the reactor vessel 12, where they may be drawn off in one of the upper product lines.

According to one embodiment of the invention, the components of the present column are configured such that methanol is produced from the reaction vessel. Product lines 36, 35, 34, 33, and 32 each draws primarily methanol. Coming off top line 31 will be gaseous by-product materials, comprising methane, ethane, propane and butane. When methanol is drawn off in a gaseous state, product line 31 may also include methanol. It should be understood that other embodiments of the present invention may contain a number of product lines different from that just described.

According to one embodiment of the present invention, the reaction vessel is operated such that methanol is refluxed upwards and heavier by-products fall to the bottom of the reaction vessel. In this embodiment, the reaction vessel may be used without intermediate trays. When the reaction vessel is used without intermediate trays, a packing material may be below the catalyst material in a reaction chamber, such that the bottom of the reaction chamber is defined by the packing material. Methanol may be collected through intermediate product lines, e.g. lines 32–36, by condensation upon cooling.

$H_2$/carbon oxide mixtures suitable as a feedstock for conversion to alcohols according to the process of the preferred embodiment can be obtained from light hydrocarbons such as methane by means of steam reforming, partial oxidation, or other processes well known in the art. Preferably the hydrogen is provided by free hydrogen, although some alcohol synthesis catalysts have sufficient water gas shift activity to convert some water to hydrogen for use in the alcohol synthesis process, respectively. It is preferred that the molar ratio of hydrogen to carbon monoxide in the feed be greater than 0.5:1, preferably from about 0.67:1 to 10:1, more preferably from about 0.67:1 to 2.5:1. More preferably, the feed gas stream contains hydrogen and carbon monoxide in a molar ratio of between about 2:1 and 4:1. The feed gas may also contain carbon dioxide. The feed gas stream should contain a low concentration of compounds or elements that have a deleterious effect on the catalyst, such as poisons. For example, the feed gas may need to be pre-treated to ensure that it contains low concentrations of sulfur or nitrogen compounds such as hydrogen sulfide, ammonia and carbonyl sulfides.

The alcohol synthesis process is typically run in a continuous mode. Typical operating conditions for methanol synthesis and higher alcohol synthesis are given in Tables 4 and 5, respectively of G. Alex Mills, Fuel, vol. 73, pages 1243–1279, 1994, hereby incorporated herein by reference.

As feed lines 21–24 deposit syngas materials into a given reaction chamber 51–55, simultaneous operations of reaction and separation take place. In the presence of catalyst material, the syngas reactants form at least one alcohol. In each reaction chamber 51–55, the materials present are also subjected to the physical affects caused by the temperature in the reaction chamber. With respect to the alcohols, if the temperature at a given point in the column is above a particular alcohol's boiling point, the molecules of that alcohol will vaporize and become gaseous. Other heavier alcohols will remain as liquids. Gravitational forces will thus act to physically separate the liquids and gases such that the gases will rise to the top of each reaction chamber 51–55 and liquids will remain at the bottom. Thus, in each reaction chamber 51–55, the temperature may be selected so as to control the amount of product that vaporizes or remains liquid.

In operation, liquids formed in one reaction chamber 51–55 will migrate in a downward direction, toward the next lower reaction chamber. Gases formed in one reaction chamber 51–55 will conversely migrate in an upward direction toward the next upper reaction chamber. Once a molecule has migrated from one reaction chamber 51–55 to another reaction chamber 51–55, this molecule will thereupon be subject to further reaction and physical separation according to the configuration present in the new reaction chamber. By a succession of such operations, the catalytic distillation reactor achieves its simultaneous objectives of reaction and separation. Further, by a succession of such operations, particularly with intermediate methanol removal, as described above, overall carbon oxide conversion beyond the thermodynamic limit may be achieved. This thermodynamic limit is known within the art and depends on conditions of temperature and pressure. It is described, for example in the article by F. Marschner and F. W. Moeller, in Applied Industrial Catalysts, Volume 2 (Academic Press, 1983), pages 215–243, hereby incorporated herein by reference. By way of illustration and not limitation, with a 50% conversion in each of four reaction chambers in the reaction vessel described above, an overall conversion of 94% may be achieved. The present method has the advantage that the high conversion is achieved in a single reactor, thus lowering the total number of reactors.

In a reaction chamber configured so as to contain a fixed bed catalyst material, the reaction step occurs in and around the fixed bed in a manner similar to that found in fixed bed alcohol reactors. Fixed bed alcohol synthesis catalyst materials may include a monolithic support material in which are present the active catalyst components along with the necessary activators and promoters. The support material provides the structure of the catalyst material. In this configuration, the catalyst material does not move. The support material will have interstices and voids through which the reactants and products may migrate into and out of the catalyst material. As stated above, the catalyst bed may be structured so that it does not occupy the entire volume of the reaction zone.

In a reaction chamber configured to contain a fluidized bed of catalyst material, the reaction step takes place throughout the area containing the fluidized bed and in a manner similar to that found in fluidized bed alcohol reactors. A fluidized bed for alcohol synthesis typically consists of solid/gas phases. The catalyst material is present as a solid. The solid catalyst material consists of loosely separated particles that are of a size and mass chosen so that they may be entrained by the gases passing upward through the reaction chamber. In operation, the particles comprising the catalyst material are turbulently mixed by the entraining gases.

In a reaction chamber configured to contain a solid/liquid slurry catalyst material, the reaction will occur in a manner similar to that found in alcohol synthesis reactors containing a solid/liquid slurry. A solid/liquid slurry for alcohol synthesis typically consists of solid-liquid phases. The catalyst material is again present as a solid. The solid catalyst material consists of separate particles that are of a size and mass chosen so that they may be slurried by the liquids passing through the reaction chamber.

Figure 4:
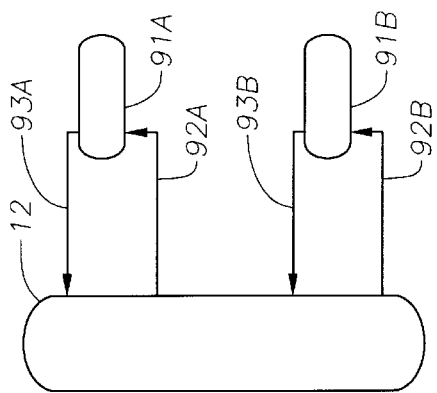
FIG. 4 is a schematic view of a third alternative embodiment of the present reaction vessel having external heat exchange lines and heat exchangers.

Referring now to FIG. 4, a preferred embodiment of the present invention includes heat exchangers 91A, 91B that are external to the column. In this embodiment, heat removal may be achieved by first drawing fluids from reaction vessel 12 through a series of heat exchange lines 92A and 92B. Heat exchange lines 92A and 92B lead from various reaction chambers 51–55 in reaction vessel 12 to one or more heat exchangers 91A and 91B. The heat exchangers are positioned externally from the catalytic distillation reaction vessel 12. Heat exchangers 91A and 91B may be selected from any of a wide variety of heat exchangers commercially available. While in one preferred embodiment, heat exchange lines 92A and 92B are attached to the reaction vessel 12 so as to draw fluids from two of the reaction chambers 51–55 of FIG. 1, other heat exchange line arrangements may be designed. For example, in another embodiment, the number of heat exchange lines may be varied and the heat exchange lines positioned differently. Also by means of illustration and not limitation, heat exchange lines may draw fluids from each reaction chamber 51–55. The heat exchange lines 92A and 92B may draw either liquids or gases from the reaction chambers 51–55. Return lines 93A and 93B, leading from heat exchangers 91A and 91B, direct cooled fluids back into reaction vessel 12. In one preferred embodiment, a return line is linked to each of reaction chambers 51–55, although other embodiments are possible without departing from the scope of the present embodiment. The fluids, that are returned to the reaction vessel 12 in this embodiment, may as shown in FIG. 4 but need not be, returned to the same reaction chamber 51–55 from which they were drawn. The fluids present in the reaction chamber therefore constitute the heat exchange medium in an external heat exchange process. Accordingly, heat exchange equipment internal to the reaction vessel 12 is eliminated or minimized. The removal of heat by external heat exchangers in accordance with the present embodiment thus also allows control of the temperatures in specific reaction chambers 51–55 by removing fluids from a specific reaction chamber 51–55 and returning the cooled fluids to the same reaction chamber. It is therefore possible to control the temperature in individual reaction chambers 51–55 by providing heat exchange equipment for that reaction chamber.

Figure 5:
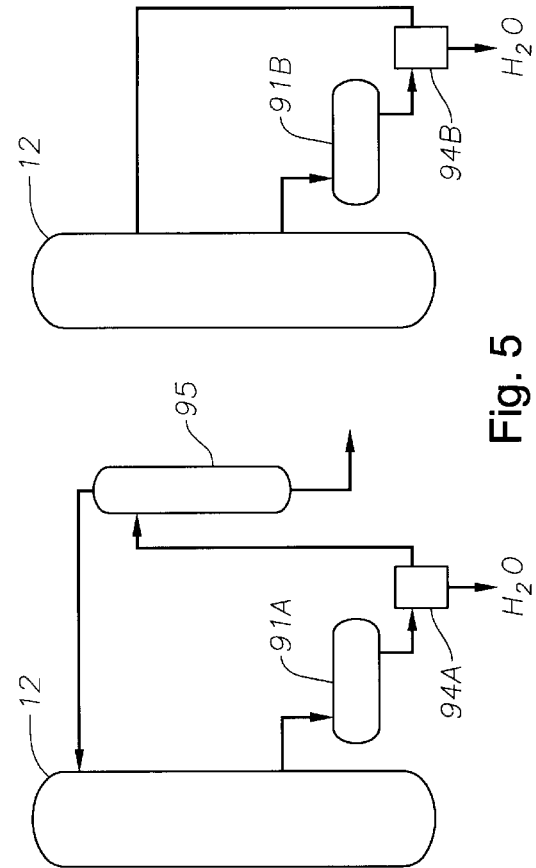
FIG. 5 is a schematic view of a fourth alternative embodiment of the present reaction vessel having external heat exchange lines, heat exchangers, water separation stages, paraffin separation stages and return lines.

Another embodiment of the invention includes one or more water separation stages. The water separation stage may follow one of several designs. In a preferred embodiment, the water separation stage may be a settling tank wherein water and hydrocarbons settle and separate. Referring to FIG. 5, water separation is achieved by pumping materials into water separation tanks 94A and 94B. When the fluids are condensed to liquid form, the water will physically separate from the liquid hydrocarbons. Once the water has separated, it can be pumped off; the remaining hydrocarbons can then be directed to an appropriate location. The hydrocarbons may either be fed back to the reaction vessel or to a product tank. Water separation may also occur in a flash separation drum. In a preferred embodiment, the water separation occurs in conjunction with the heat removal operation. Referring again to FIG. 5, fluids drawn from reaction vessel 12 are first passed through heat exchangers 91A or 91B. Upon cooling, hot fluids will condense, or partially condense, to liquid form. The fluids next pass to water separation tanks 94A and 94B. It is there that water physically separates from other liquids and can be removed.

In another embodiment (not shown), water separation may also be achieved in conjunction with fluid recycle and reflux. In this embodiment, fluids pumped through the recycle and reflux lines are again passed into a water separation tank. Once the liquids have separated in the water separation tank, the water layer may be pumped off. When recycling fluids from the top of the reaction vessel, the fluids may first pass through a heat exchanger or condenser to cool the fluids. The fluids may then pass into a water separation tank. When refluxing fluids from the bottom of the reaction vessel the fluids may also pass through water separation tanks that will separate out water. Refluxed fluids can themselves be cooled or reheated.

Other embodiments of the invention may also include the use of the reaction vessel for the production of alcohols. Further, an embodiment may include one or more paraffin separation stages. Referring to FIG. 5, paraffin separation is achieved by pumping materials into a paraffin separator 95. The paraffin separator itself may follow a membrane separation process, a chemical separation process, or be a multi-stage distillation column. The paraffin separator should be designed so as to separate paraffins from olefins. The paraffins, which are no longer reactive in the alcohol synthesis, may then be removed to product storage. The olefins may be returned to the reaction vessel for further Fischer-Tropsch reaction. Paraffin separation may also take place during recycle and reflux operations. In such an embodiment fluids pumped through the recycle and reflux lines will pass through a water separation stage and then a paraffin separation stage. In this manner, reactive olefins can be separated from the non-reactive paraffins. The olefins may be returned to the reaction vessel in the recycle and reflux return lines.

A variety of standard control equipment and measurement devices will assist in the operation of the catalytic distillation reactor. Thermocouples or other temperature measuring devices may be positioned within the reaction vessel 12. Preferably, a plurality of temperature measuring devices may be present at different positions in each reaction chamber such as reaction chambers 51–55 of FIG. 1. In this manner the temperature in each particular reaction chamber 51–55 may be measured and/or monitored. Hot spots, cool spots, temperature spikes and excessive temperature gradients typically should be avoided. Thus, by careful temperature measurement, the proper temperature differential may be maintained between adjacent reaction chambers 51–55 in order to promote the optimum mass transfer between the reaction chambers.

Flow regulators, not shown, typically control the passage of alcohols through feed lines 21–24, product lines 31–37, recycle and reflux lines 81, 82 and heat exchanger lines 92A, 92B, 93A and 93B. Flow regulator equipment may include valves, which may be either manual or automatic. In addition, fluid flows may be measured with standard measuring devices such as manometers and flow meters.

The present method has the advantage that a single reaction vessel may be optimized for the production of a selected product or range of products according to the catalyst materials selected and the process conditions selected. Thus, a single reaction vessel may alternately be loaded with different catalysts materials. For example, hydrocarbons may be produced in the reaction vessel using catalyst materials selective for the production of hydrocarbons, for example by the Fischer-Tropsch synthesis. Alternately, the same reaction vessel may be used for the production of methanol using catalyst materials selective for the production of methanol. Still alternately, the same reaction vessel may be used for the production of higher alcohols.

Without further elaboration, it is believed that one skilled in the art can, using the description herein, utilize the present invention to its fullest extent. While a preferred embodiment of the invention has been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

We claim:

1. A method for the synthesis of at least one alcohol comprising;
    injecting reactants into a catalytic distillation reactor and removing alcohol products from said catalytic distillation reactor, wherein the catalytic distillation reactor comprises:
        a reaction vessel having a plurality of distillation zones and a catalytic material in each of said distillation zones.

2. The method according to claim 1 wherein said reaction vessel further comprises a plurality of trays, wherein said trays as substantially perpendicular to the axis of said reaction vessel.

3. The method according to claim 1 wherein said reaction vessel further comprises a plurality of trays, wherein said trays are position at an incline with respect to the axis of said reaction vessel.

4. The method according to claim 1 wherein at least one of said distillation zones comprises a tray with at least one of the following: bubble caps, weirs, filters, sieves, or sintered metal sieves.

5. The method according to claim 1 wherein at least one of said catalyst materials comprises a catalyst selected from the group consisting of Cu-Zn alloys, Cu-rare earth alloys, Group 8 elements, Group 9 elements, and Group 10 elements, and combinations thereof.

6. The method according to claim 5 wherein said at least one catalyst material further comprises a promoter selected from the group consisting of Cr, Al, Mn, V, Mo, Ag, alkali metals, and combinations thereof.

7. The method according to claim 5 wherein said at least one catalyst material further comprise a catalyst support.

8. The method according to claim 1 wherein said catalyst materials are in the form of at least one of the following: particles, pellets, monoliths, honeycombs, packed bed, foams, or aerogels.

9. The method according to claim 1 wherein said catalyst materials substantially completely fill said distillation zones.

10. The method according to claim 1 wherein said catalyst materials do not substantially completely fill said distillation zones.

\* \* \* \* \*